United States Patent [19]

Ito

[11] 4,058,460
[45] Nov. 15, 1977

[54] HORIZONTAL FLOW-THROUGH COIL PLANET CENTRIFUGE WITHOUT ROTATING SEALS

[75] Inventor: Yoichiro Ito, Bethesda, Md.

[73] Assignee: The United States of America as represented by the Department of Health, Education and Welfare, Washington, D.C.

[21] Appl. No.: 778,455

[22] Filed: Mar. 17, 1977

[51] Int. Cl.² .................................................. B01D 15/08
[52] U.S. Cl. .................................... 210/198 C; 210/31 C
[58] Field of Search .............. 210/31 C, 198 C; 55/67, 55/197, 386

[56] References Cited
U.S. PATENT DOCUMENTS 3,775,309  11/1973  Ito et al. ............................ 210/31 C
3,856,669  12/1974  Ito et al. ............................ 210/31 C Primary Examiner—John Adee
Attorney, Agent, or Firm—Browdy and Neimark

[57] ABSTRACT

An apparatus for countercurrent chromatography consisting of a horizontal helical column array which is rotated about its own axis and simultaneously is rotated around a stationary central horizontal pipe at the same angular velocity to prevent twisting of its inlet and outlet flow tubes, which extend through the stationary central horizontal pipe. The column array is parallel to the stationary central pipe. The planetary motion allows both gravity and centrifugal force acting at respective times to provide high efficiency analytical and preparative scale separations on a broad spectrum of two-phase systems.

10 Claims, 6 Drawing Figures

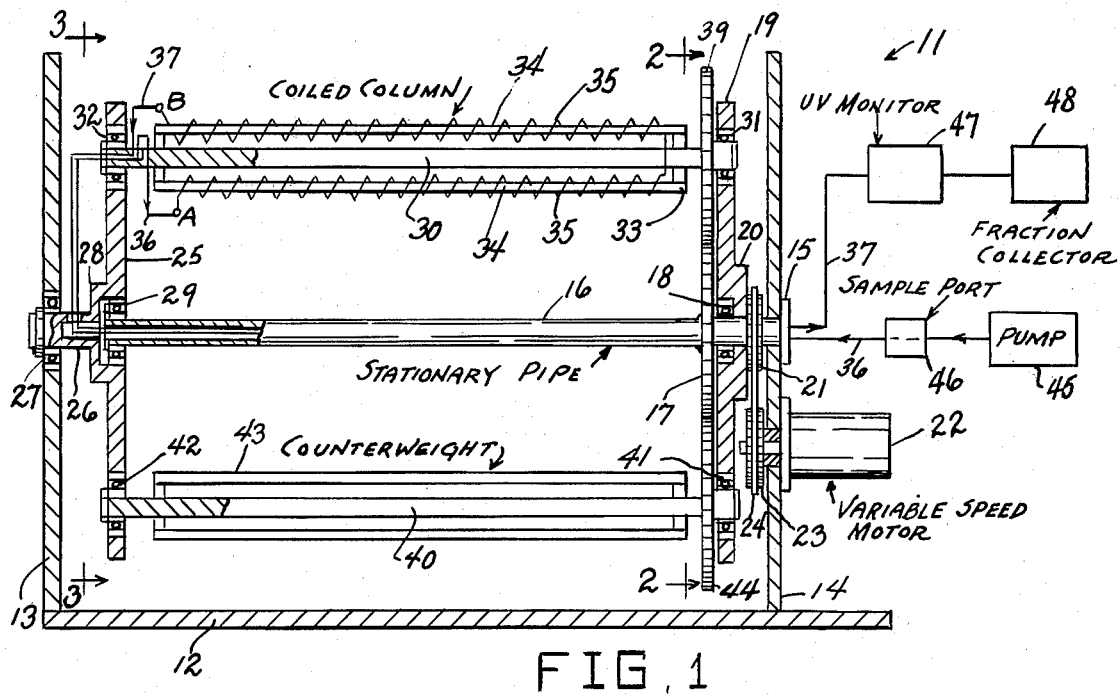
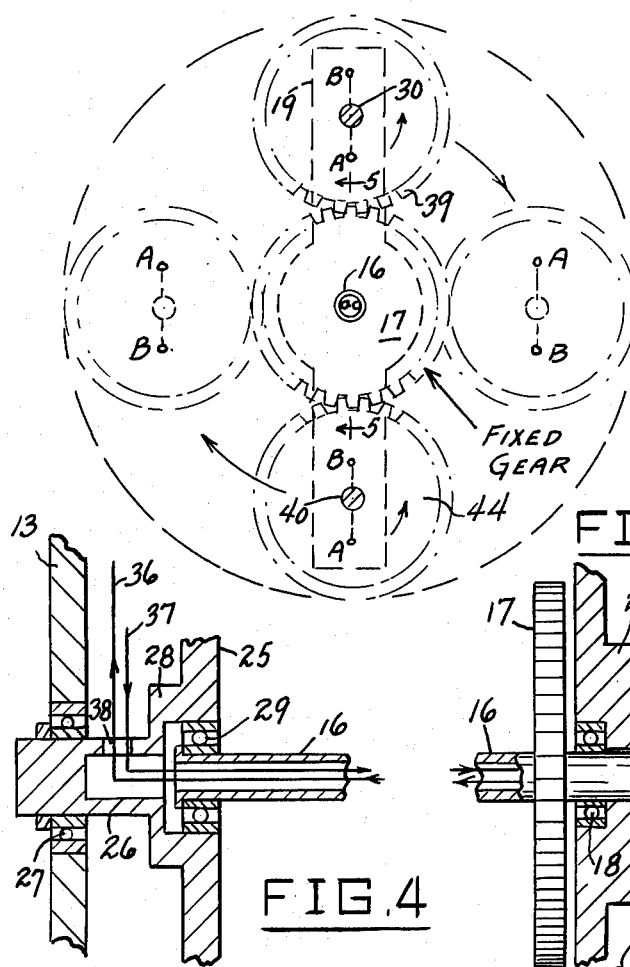
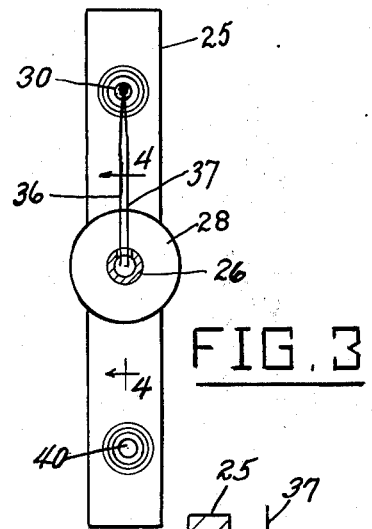
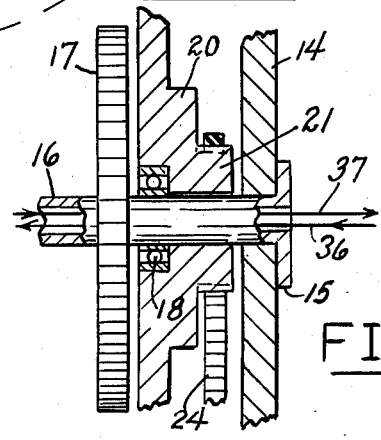
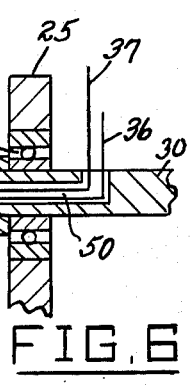

HORIZONTAL FLOW-THROUGH COIL PLANET CENTRIFUGE WITHOUT ROTATING SEALS

FIELD OF THE INVENTION

This invention relates to the separation of samples in two-phase solvent systems, and more particularly to a system for continuous countercurrent chromatography of the type employing a horizontal coiled helical tubular array rotating on its longitudinal axis.

BACKGROUND OF THE INVENTION

Centrifugal countercurrent chromatography has been successful in high efficiency analytical separation with a variety of two-phase solvent systems. For example, see Y. Ito and R. L. Bowman, (1975) Anal. Biochem., 65,310; Y. Ito and R. L. Bowman, U.S. Pat. No. 3,856,669, Dec. 24, 1975; and Y. Ito and R. L. Bowman, U.S. Pat. No. 3,775,309, Nov. 27, 1973. In these systems, two immiscible or partially soluble liquid phases are brought into contact for the transfer of one or more components. In helix countercurrent chromatography, a horizontal helical tube is filled with one phase of a two-phase liquid and the other phase is introduced at one end of the helix and passes through to the first phase. In these systems, to enable the countercurrent process to take place inside a very small-diameter tube having a maximum number of turns, it is desirable to enhance the gravitational field by the use of centrifugation.

As reported, for example, in Y. Ito and R. L. Bowman, Science, 173, 420 (1971), a rotating helical column in an acceleration field has a capability of retaining the stationary phase as the mobile phase continuously elutes through the column. Consequently, solutes locally introduced are subjected to an efficient partition process and are separated according to their relative partition coefficients. The flow-through coil planet centrifuge technique in certain circumstances has yielded an efficiency up to 10,000 T.P. with a fine analytical column in a strong centrifugal force field, while in other circumstances efficient preparative scale separations have been successful with a slowly rotating helical column in the gravitational field. It would be desirable to have a system able to deal with a wide inclusive range of such circumstances, wherein the helical column array rotates with respect to both gravitational and centrifugal force fields.

Further background will be given by examining the following U.S. prior patents, which appear to represent the closest prior art relating to the present invention, found in the course of a preliminary search:
Ito et al, U.S. Pat. No. 3,775,309
Ito et al, U.S. Pat. No. 3,856,669
Ito, U.S. Pat. No. 3,994,805.

SUMMARY OF THE INVENTION

Accordingly, an object of the invention is to provide for improved chemical separations.

Another object of the present invention is to provide a novel and improved preparative countercurrent chromatographic system wherein the helical column array rotates with respect to both gravitational and centrifugal force fields.

A further object of the present invention is to provide an improved countercurrent chromatographic system employing a horizontal rotating column array which does not require rotating seals.

A still further object of the invention is to provide an improved countercurrent chromatographic system employing a horizontal helical column array rotating around its own axis and around a stationary tubular protective conduit housing member through which extend the inlet and outlet conduits of the column array, the helical column array rotating around the said member in a planetary mode and at a rate so as to avoid twisting of the inlet and outlet conduits.

A still further object of the invention is to provide an improved apparatus for countercurrent chromatography using a horizontal helical column array which rotates about its own axis and simultaneously revolves around the central axis of the apparatus at the same angular velocity to prevent twisting of the associated flow conduit tubes, and wherein the planetary motion of the array allows both gravity and centrifugal force to perform high efficiency analytical preparative scale separations over a broad spectrum of two-phase systems, such as separation of DNP amino acids with $CHCl_3/CH_3COOH/0.1N$ HCl (2:2:1).

In furtherance of these and other objects, the following discussion generally explains an embodiment according to the present invention:

The separation column assembly comprises a helical column array horizontally supported by a rotatable frame having a mobile gear. The mobile gear meshes with an identical stationary gear mounted on the central axis member of the apparatus, which comprises a stationary pipe. The feed and return tubes of the helical column array are led through the end portion of the mobile gear shaft and through the stationary pipe and are tightly supported thereby, concentric with the stationary gear. Rotation of the mobile gear around the stationary gear gives the helical column array a planetary motion, namely, revolution around the central axis of the apparatus and rotation about its own axis at the same angular velocity. Thus, during one complete revolution of the mobile gear, the helical column array rotates twice with respect to the gravity field and once with respect to the centrifugal force field introduced by the revolution. This planetary motion prevents twisting of the flow tubes as they rotate with the mobile gear.

The unique capability of the system of the present invention derives from the fact that the helical column array rotates with respect to both gravitational and centrifugal force fields. When a large-bore preparative column is eluted with an extremely low interfacial tension phase system, a slow rotation of the column in the gravitational field prevents emulsification of the phases which would result in carry-over of the stationary phase. When a fine analytical column is used, a high revolutional speed can create a strong centrifugal force field that allows the two phases to counterflow through the narrow bore of the column without a plug flow, as in the flow-through coil planet centrifuge described previously in Y. Ito and R. L. Bowman, Science, 173 420 (1971).

BRIEF DESCRIPTION OF THE DRAWINGS

Further objects and advantages of the invention will become apparent from the following detailed description of an embodiment, and from the accompanying drawings, wherein:

FIG. 1 is a partly schematic view of an improved counter-current chromatography apparatus according to the present invention, showing the associated helical column array supporting assembly substantially in vertical cross-section.

FIG. 2 is a transverse vertical cross-sectional view taken substantially on the line 2—2 of FIG. 1 and showing the planetary gearing arrangement and its mode of movement.

FIG. 3 is a transverse vertical cross-sectional view taken substantially on the line 3—3 of FIG. 1.

FIG. 4 is an enlarged fragmentary vertical cross-sectional view taken substantially on the line 4—4 of FIG. 3.

FIG. 5 is an enlarged fragmentary vertical cross-sectional view taken substantially on the line 5—5 of FIG. 2.

FIG. 6 is an enlarged fragmentary vertical cross-sectional view showing the axial end passage in the column array rotary shaft for the array inlet and outlet tubes.

DESCRIPTION OF A PREFERRED EMBODIMENT

Referring to the drawings, 11 generally designates a typical countercurrent chromatography apparatus according to the present invention. The apparatus 11 comprises a supporting base 12 which may be rigidly secured on a suitable horizontal surface. Base 12 is provided with spaced upstanding parallel wall members 13 and 14. Rigidly secured at 15 to upstanding wall member 14 is a horizontal pipe 16 extending perpendicularly toward the opposite upstanding wall member 13. Rigidly secured on pipe 16 adjacent to but spaced from wall member 14 is a stationary sun gear 17.

Journalled on pipe 16 adjacent gear 17 by a wall bearing assembly 18 is a first rotary arm 19 having a central hub portion 20 provided with a gear member 21. An electric drive motor 22, preferably of the variable speed type, is suitably mounted on upstanding wall 14 and is provided with a drive gear 23 which is drivingly coupled to gear member 21 by a toothed belt 24.

A second rotary arm 25 has a hollow central axle portion 26 which is journalled to upstanding wall member 13 by a ball bearing assembly 27 in axial alignment with stationary pipe 16. Arm 25 is provided with a central bearing cup portion 28 in which the end of pipe 16 is received. Cup portion 28 is journalled supportingly on the end of pipe 16 by means of a ball bearing assembly 29.

A first horizontal rotary shaft member 30 is journalled in respective end portions of arms 19, 25 by ball bearing assemblies 31, 32. Rigidly mounted on shaft member 30 is a horizontally extending elongated frame 33 including horizontal rod members 34, 34 carrying serially-connected helical column units 35, 35. An inlet tube 36 leads to the column array at A and an outlet tube 37 extends from the column array at B. Tubes 36, 37 extend through an axial end passage 50 in shaft 30 and thence through a side aperture 38 in the wall of hollow axle portion 26, and extend through stationary pipe 16, which acts as a protective housing for said tubes.

The chromatographic column array may be made either by winding Teflon tubing directly on the rotary shaft 30 or by arranging a desired number of column units 35 connected in series on horizontal support rods 34 arranged around the rotary shaft.

Rotary shaft 30 is provided adjacent arm 19 with a planet gear 39 identical to and meshing with stationary sun gear 17.

A second horizontal rotary shaft member 40 is journalled on the ends of respective arms 19, 25 opposite shaft member 30 by ball bearing assemblies 41, 42. Shaft 40 carries a suitably weighted frame 43 acting as a counterweight for the mass defined by rotary shaft 30 and the parts carried thereby. Shaft 40 is provided adjacent arm 19 with a planet gear 44 identical to and meshing with stationary sun gear 17.

The solvent may be introduced into the helical tube array by a suitable pump 45 through a sample port 46 and the feed tube 36. The eluate leaving the helical tube array via the outlet tube 37 may be continuously monitored by suitable monitoring means 47, such as an LKB Unicord III, and then may be fractionated by a fraction collector 48.

In a typical apparatus 11, the rotary arms 19, 25 hold the rotary shafts 30, 40 in the respective pairs of bearing assemblies 31, 32 and 41, 42 at a radial distance of about 15 cm. from the central pipe 16 in symmetrically opposite positions parallel thereto.

The inlet and outlet conduits 36, 37 are of the flexible type with sufficient slack to allow them to flex freely during the planetary movement of the column array caused by the rotation of arms 19, 25 by motor 22. As shown in FIG. 2, if arm 19 is rotated clockwise by motor 22, the meshing relationship of planet gear 39 with fixed sun gear 17 causes planet gear 39 to rotate clockwise around the axis of shaft 30. As a result, revolution of the helical tube array causes compensating planetary rotation of the array in the same direction, which is different from that obtained in Ito et al, U.S. Pat. No. 3,775,309. This prevents twisting of the inlet and outlet tubes 36, 37 as they rotate with the mobile gear 39.

In FIG. 2 it will be noted that a line connecting the projections of points A and B on mobile gear 39 rotates twice during one complete revolution of said mobile gear 39. Thus, during one complete revolution of said mobile gear 39 the helical column array rotates twice with respect to the gravity field and once with respect to the centrifugal force field introduced by revolution.

The flow tubes 36, 37 move past each other between passage 50 and aperture 38 during revolution of mobile gear 39. The frictional rubbing wear of the tubes 36, 37 may be minimized by coating them with suitable lubricant; such wear is further reduced by anchoring the flow tubes as close as possible to the axes of the gears 39, 17.

The mode of operation and capability of the apparatus 11 are typically demonstrated in the separation of DNP amino acids with a two-phase system composed of $CHCl_3/CH_3COOH/0.1N$ $HCl$ (2:2:1) using a short preparative column consisting of a 2.6 mm i.d., 5 m long Teflon tube coiled onto a 1.25 cm o.d. pipe to make approximately 100 helical turns. The sample solution was prepared by dissolving DNP-L-glutamic acid (partition coefficient : 1.9) and DNP-L-alanine (partition coefficient : 0.56) in the upper aqueous phase at a concentration of about 0.5g % for each component. In each separation the column was first filled with the stationary phase and 0.2 ml of sample solution was introduced through the sample port 46, followed by elution with the mobile phase at respective selected flow rates while the column was rotated at respective selected values of RPM. The eluate was continuously monitored with the LKB Uvicord III monitor 47 at 280 nm.

Thus, runs were made using flow rates of 24, 60 and 120 ml/hr and various RPM values from zero to 300

RPM, and using both upper aqueous and lower organic phases as the stationary phase. Absorbance vs. time curves were obtained, consisting of two peaks separated by a trough. In each diagram the efficiency of separation could be estimated by the relative height of the trough between the two peaks. These diagrams clearly demonstrated the effects of the gravity and centrifugal forces on partition efficiency. The efficiency increased sharply with revolution from zero to from 10 to 25 RPM, where the gravity played a major role in partition while the centrifugal force was negligibly small. When the revolutional speed reached a range of 25 to 50 RPM, the gravity force failed to retain a satisfactory amount of the stationary phase against the flow and yet the centrifugal force was not strong enough to compensate the gravity force. As a result, the efficiency declined with the depletion of the retained stationary phase, indicated by a decreased retention time of the second peak and a shortened time lapse between the two peaks at a given flow rate. Further increase of the revolutional speed up to 300 RPM resulted again in a sharp rise of efficiency, where the centrifugal force produced by the revolution played a major role in partition.

As previously stated, these two controllable operational factors (gravity and centrifugal force) enable the apparatus of the present invention to be employed with broad applicability to two-phase solvent systems. Application to phase systems with an extremely low interfacial tension and/or a high tendency of emulsification is possible by employing a slow rotation in the gravitational field, whereas the apparatus may be efficiently employed with other phase systems using a high revolutional speed for both analytical and preparative scale separations.

While a specific embodiment of an improved apparatus for countercurrent chromatography has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. In an apparatus for continuous countercurrent chromatography, a support, helical separation column means horizontally and rotatably mounted on the support, inlet and outlet flow tubes connected to said column means, fixed, elongated tube guide means on the support extending horizontally substantially parallel to and spaced from said column means and receiving said flow tubes at one end and defining a protective housing for the flow tubes, and means to simultaneously rotate said column means around its rotational axis and revolve said column means around the tube guide means at relative rates avoiding twisting of the flow tubes, whereby to simultaneously develop both gravitational force reversals and centrifugal forces in said column means.

2. In an apparatus for continuous countercurrent chromatography, a support, a conduit member horizontally rigidly mounted on said support, a pair of spaced parallel arm members, means rotatably supporting said arm members on said conduit member perpendicularly thereto, helical horizontal separation column means journalled between said arm members in spaced parallel relation to said conduit member, inlet and outlet flow tubes extending through said conduit member and being connected to said column means to define a flow path therethrough, and means to simultaneously rotate said column means around its rotational axis relative to said arm members and to revolve said arm members around said conduit member at relative rates avoiding twisting of the flow tubes, whereby to simultaneously develop gravitational force reversals in the column means caused by rotation of the column means relative to said arm members as well as the gravitational and centrifugal force effects caused by the revolution of said column means around said conduit member.

3. The apparatus of claim 2, and horizontal counterweight means connected to said arm members symmetrically opposite said helical separation conduit means.

4. The apparatus of claim 3, and means to rotate said counterweight means relative to said arm members synchronously with the rotation of said helical separation conduit means.

5. The apparatus of claim 2, and wherein the means to simultaneously rotate the column means and revolve the arm members comprises a sun gear rigidly secured on the conduit member, a planet gear on the column means meshing with said sun gear, and means to drive the planet gear around the sun gear.

6. The apparatus of claim 5, and wherein said drive means comprises motor means on the support and means drivingly coupling said motor means to one of the arm members.

7. The apparatus of claim 5, and wherein said planet gear and said sun gear are identical.

8. The apparatus of claim 5, and wherein the other arm member is provided with a cup portion rotatably receiving said conduit member, said cup portion having a hollow axle element journalled on said support coaxially with said conduit member.

9. The apparatus of claim 8, and wherein said inlet and outlet flow tubes extend into said hollow axle element, said axle element having an aperture through which the flow tubes extend for connection to said column means.

10. The apparatus of claim 9, and wherein said column means is provided with a rotary supporting shaft having an axial end passage through which said flow tubes extend.

* * * * *